United States Patent [19]

Gardineer et al.

[11] Patent Number: 5,329,927
[45] Date of Patent: Jul. 19, 1994

[54] APPARATUS AND METHOD FOR LOCATING AN INTERVENTIONAL MEDICAL DEVICE WITH A ULTRASOUND COLOR IMAGING SYSTEM

[75] Inventors: Bayard Gardineer, Skillman; David Vilkomerson, Princeton, both of N.J.

[73] Assignee: Echo Cath, Inc., Monmouth Junction, N.J.

[21] Appl. No.: 22,112

[22] Filed: Feb. 25, 1993

[51] Int. Cl.⁵ .................................. A61B 8/12
[52] U.S. Cl. .................. 128/660.03; 128/662.05; 128/662.03
[58] Field of Search .............. 128/660.03, 660.02, 128/662.03, 660.09, 662.05, 662.06; 73/599, 602

[56] References Cited

U.S. PATENT DOCUMENTS

| | | | |
|---|---|---|---|
| 3,805,596 | 4/1974 | Klahr | 128/660.09 |
| 3,921,622 | 11/1975 | Cole | 128/662.03 |
| 4,217,516 | 8/1980 | Iinuma et al. | 128/662.03 |
| 4,461,178 | 7/1984 | Chamuel | 73/599 |
| 4,819,649 | 4/1989 | Rogers et al. | 128/660.02 |
| 5,076,278 | 12/1991 | Vilkomerson et al. | 128/662.03 |
| 5,095,910 | 3/1992 | Powers | 128/662.05 |

*Primary Examiner*—William E. Kamm
*Assistant Examiner*—George Manuel
*Attorney, Agent, or Firm*—Plevy & Associates

[57] ABSTRACT

A VIBER vibrating mechanism is coupled to a cannula or needle and operates to provide flexural vibrations to move the needle and to enable detection of the position of a needle within a body of interest by a color ultrasound imaging system. The VIBER mechanism exhibits multiple modes of oscillation when energized. The VIBER mechanism is excited to exhibit predetermined oscillations at a given frequency in the X plane, a predetermined oscillation at another frequency in the Y plane and still another frequency of oscillation in the Z plane. In this manner, the VIBER mechanism device exhibits motion in all three planes, which motion is detectable by a conventional color ultrasound imaging system. The frequency of oscillation is a function of the entire system, namely the VIBER mechanism, the needle or cannula which is attached to the VIBER mechanism and the tissue. The resonant frequency is preferred as it provides larger vibrational amplitudes. In this manner, a resonant frequency is controlled by means of a feedback control loop, whereby the frequency applied to the VIBER mechanism is monitored to determine resonance and is held at the resonant frequency as the VIBER mechanism or needle is moved. The vibration in the representative planes causes a typical conventional color ultrasound imaging system to display the vibration or movement by means of a color variation. By viewing the display, a system operator, such as a physician can visualize the location of the needle because of the color indication provided by the display.

23 Claims, 8 Drawing Sheets

FIG. 4a  860 HERTZ

FIG. 4b  1305 HERTZ

FIG. 4c  2840 HERTZ

APPARATUS AND METHOD FOR LOCATING AN INTERVENTIONAL MEDICAL DEVICE WITH A ULTRASOUND COLOR IMAGING SYSTEM

FIELD OF THE INVENTION

The present invention relates to ultrasonnet imaging systems and more particularly, to the detection and display of the location of an interventional medical device by a color ultrasonic imaging system through detection of motion causing a Doppler shift.

BACKGROUND OF THE INVENTION

As is well known in the medical profession, ultrasonic imaging is utilized to enable a physician to view an internal area of a patient's body that is of concern to the physician. For example, ultrasonic imaging is utilized in procedures such as the biopsy of possibly malignant tumors, and so on. In a biopsy procedure, an interventional medical device, such as a biopsy needle, is inserted into the patient and moved to the internal area imaged by an ultrasonic imaging system. It is an objective during such procedures for the physician to clearly visualize tint needle arid therefore monitor the movement of the needle through the body as it approaches the tissue masses for removal by the biopsy needle.

There are various approaches, employing various means, to enable a user to view the movement of a needle as it is guided through a patient's body or otherwise. Particular reference is made to U.S. Pat. No. 5,095,910 entitled ULTRASONIC IMAGING OF BIOPSY NEEDLE issued on Mar. 17, 1992 to Jeffry E. Powers (the '910 patent). This patent describes a system for imaging a biopsy needle with ultrasound, wherein the needle causes a Doppler response in a color ultrasonic imaging system through controlled, highly directional motion produced by the reciprocation of the needle tip. The '910 patent describes a biopsy needle which includes a hollow cannula that carries a removable stylet. There are shown means for reciprocating the stylet which is coupled to the proximal end of the stylet and the distal tip of the stylet is reciprocated at the distal end of the cannula. This motion is a reciprocal motion that is detected through Doppler interrogation of the imaged body region at which the biopsy is being performed. The Doppler shift occurring at the needle tip is detected and displayed in the image of the body region being scanned by the color ultrasonic imaging system. This allows the needle tip to be monitored as it approaches the tissue to be biopsied. This particular apparatus is described in conjunction with a color flow imaging system such as that employed in the Ultramark 9 colorflow imaging system available from Advanced Technology Laboratories, Inc., of Bothell, Wash. In any event, the apparatus described attempts to reciprocate a biopsy needle over a relatively wide range of frequencies and the reciprocation of the needle tip results in a Doppler shift which is detectable by the ultrasonic imaging system, via Doppler signal interrogation.

As indicated above, the '910 patent depicts the use of reciprocating motion along the axis of a needle by the stylet (the inner, solid element within the hollow tube which is the outside of the needle, the cannula). This method depends upon the tip of the stylet extending out from the cannula, and moving the tissue near the tip. This motion is detected by the colorflow imaging system and shown as color. The described method, therefore, only shows the tip of the needle, and will not show the tip if the tissue is liquid, such as the necrotic center of tumors, or at right angles to the ultrasound beam. In the described method, a driver is in the hub of the needle, requiring specially prepared needles or other such devices for use in the described system.

Other methods also utilize ultrasound imaging techniques which are well suited for soft tissue analysis. In this regard, reference is made to U.S. Pat. No. 5,076,278 entitled ANNULAR ULTRASONIC TRANSDUCERS EMPLOYING CURVED SURFACES USEFUL IN CATHETER LOCALIZATION, which issued on Dec. 31, 1991 to Vilkomerson, et al. This patent discloses an annular ultrasonic transducer that is sensitive over a broad range of angles of incident acoustic beams and which is mounted on a catheter or other medical device. By utilizing an ultrasonic imaging system, the position of the transducer on the catheter during ultrasonic scanning modes can be ascertained and incorporated into the image generated by the imaging system. As in the case of the system described in the '910 patent, only one point of the medical device is detected and displayed.

The color ultrasound imaging described in the '910 patent is a relatively new form of ultrasound imaging. Reference is also made to an article entitled "Medical Ultrasonic Imaging—State or The Art and Future", Electro-International Conference Record, Region 1, Central New England (Council, METSAC, IEEE and New England and New York Chapters, ERA, Apr. 16–18, 1991, pp. 64–65 by Vilkomerson, D., Gardineer, B., and Lyons, D for background information on color ultrasound imaging.

Color imaging has also been utilized in ultrasound systems used to measure blood velocity. The prior art recognizes that moving blood cells reflect ultrasonic energy that is Doppler shifted in frequency. Therefore, the velocity of the blood may be measured by utilizing an ultrasound imaging system. Moreover, ultrasound imaging systems have been utilized to locate the best point in a blood vessel in which to measure blood velocity by measurement of the Doppler shift. The Doppler shift in back-scattered ultrasound at a point in a blood vessel is measured by the detection of quadrature time samples of the back-scattered signal. This technique entails the monodyne detection of the signal in conjunction with sine and cosine mixing at a transmitted frequency in order to detect real and imaginary parts of a signal vector at a sampling time. The signal vector, which is a sum of the individual signal vectors from each blood cell, changes slowly (assuming the blood cells stay in the same relative positions) but advances or retreats in phase depending upon whether the blood cells are coming toward a transducer or away.

Figure 1:
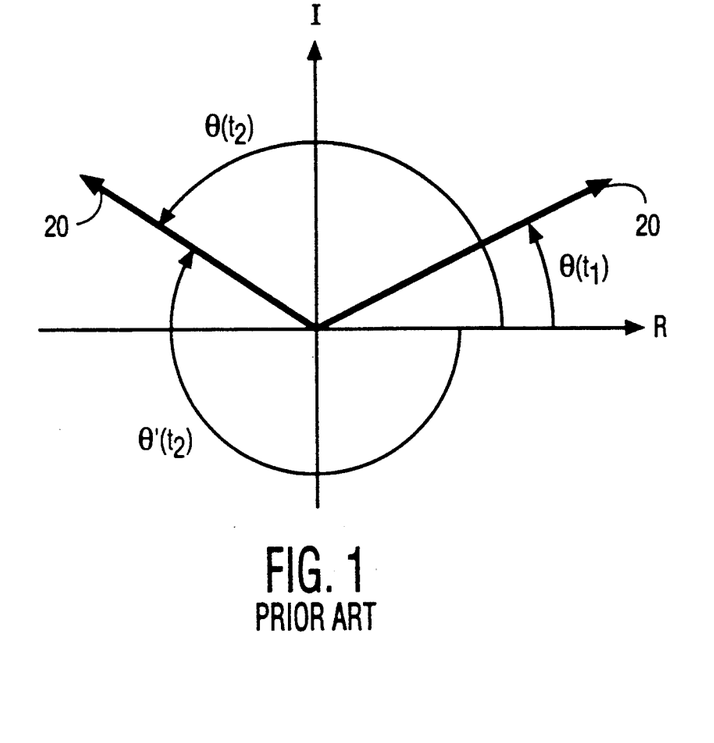
FIG. 1 is a graphical representation depicting measurements in time of two signal vectors and useful in describing the operation of the present invention.

FIG. 1 (prior art) shows the result of two measurements in time of a signal vector 20. If the signal vector 20 is obtained at time $t_1$, and after a time t the signal vector 20 is obtained from the same blood sample at time $t_2$, the signal vector 20 will have advanced, in a counterclockwise direction, from $\theta(t_1)$ to $\theta(t_2)$. Continued measurements of the signal vector show that the signal vector rotates at a rate $f_d$, which can be shown to be a Doppler frequency as calculated by a standard physics formula. The Doppler frequency or frequencies can then be analyzed by a spectrum analyzer in order to show the distribution of blood velocities as a function of time. However, Doppler information over the entire image frame is not provided with this technique. Furthermore, the Doppler ultrasound signal path is independent of the image ultrasound signal path.

In order to overcome these deficiencies, the prior art noted that the measurements depicted in FIG. 1 are enough to determine the blood velocity. The phase shift shown in FIG. 1 is proportional to the distance in wavelengths that the blood cells have moved. In addition, since the time interval between measurements is known, dividing the distance that the blood vessels have moved by the time interval between measurements yields the blood velocity. Since two samples at a point in a blood vessel were sufficient to calculate blood velocity, imaging pulses are then employed to determine blood velocity. Therefore, the velocity of the blood cells could be determined at every point in the ultrasonic image display. Furthermore, in the known blood velocity system, the velocity of the blood cells is provided on an image display with the pixels in the image display colored as a function of the velocity of the blood cells at every point.

Color ultrasound imaging systems are sensitive to the relatively small motion of blood in arteries, to displacements measured in microns. Typical state of the art systems are able to show velocity in the 1 to 100 centimeters per second (cm/sec) or more range on a color image display. In order to accomplish this, the first and second imaging pulses are produced every 80 to 330 microseconds ($\mu$sec) depending on the scale of the velocity to be detected. If a 5 cm/sec velocity is detected where the sampling interval of the imaging pulses is 118 $\mu$sec, the displacement of the point is 5 cm/sec times 118 $\mu$sec, or approximately 6 microns. Therefore, small vibratory motions, on the order of microns, are detectable by color flow imaging.

Furthermore, there are commercially available needles with grooved tips, (e.g., the Echotip from W. Cook and Co.), to reflect ultrasound better to attempt to make the needles more visible in an ultrasound image.

In terms of additional background, some years ago physicians noticed color images appearing when needles were advanced through tissue (McNamara, M. P., *AJR* 152, p. 1123 (1989), Kurohiji et al., *J. Ultrasound Med* 9: pp. 243-245, 1990). Kimme-Smith et al., in a paper given at the AIUM, in February 1991 (see abstract in *Journal of Ultrasound in Medicine*, Volume 10, Number 3, p. 64) described making a needle visible on a colorflow imaging system by using a 400 Hz buzzer, an extension of the previous observations. The impression given in the Kimme-Smith article is that the buzzer acts in a reciprocating motion in the same manner as is done by hand, although the article is not clear on what exactly was done. The authors do not report consistent visualization using their method.

SUMMARY OF THE INVENTION

The present invention is directed to a method and apparatus for causing a periodic or oscillating mechanical motion in an interventional medical device. The oscillatory nature of the mechanical motion results in a significant Doppler shift effect that is readily detected by a color ultrasonic imaging system to provide a clear color image of the device within the area of a patient scanned and displayed by the imaging system. The present invention utilizes the sensitivity of known color ultrasonic imaging systems to micron sized vibrations as a basis for providing a detectable presence of an interventional device for imaging the device. Micron sized oscillatory distortions permit a color ultrasonic imaging device to detect anti display a colored image of the device within a grayscale image of surrounding tissue.

Generally, the present invention comprises a mechanical motion mechanism controllably activated to periodically move through preselected mechanical positions. A mechanical coupling element is mounted on the mechanical motion mechanism and coupled to an interventional device for transmitting mechanical energy generated by the periodic motions as an oscillating force to the interventional device. Pursuant to the present invention, the preselected mechanical positions and oscillatory nature of the motions are arranged and configured to transmit the mechanical energy produced by the periodic motions via the coupling element as flexural waves that propagate along the length of the interventional device.

Flexural waves are a known form of vibrational motion that occurs in rod-like elements under certain circumstances. Rod-like elements are a typical configuration for interventional medical devices such as, e.g., needles and guidewires. Flexural waves exhibit characteristics similar to standing or propagating waves. For example, the mechanical motion transmitted to the interventional medical device can be controlled to cause micron sized mechanical distortions along the entire length of the device that exhibit a sinusoidal wave shape. The sinusoidal wave shape causes a series of Doppler shifts along the length of the transmitted flexural wave as a function of the periodically changing peaks and valleys of the sinusoidal wave shape.

Moveover, the mechanical motion mechanism can be controlled to transmit the mechanical motions in specific axial modes so that, e.g., the flexural waves propagate along one or more specific axes of the rod-like shape of the interventional device. Thus, the mechanical motion mechanism can be configured and controlled to cause flexural waves to propagate along one or more of the X, Y and Z axes of the device. In addition, highly efficient flexural wave generation along preselected axes of the device can be achieved by fixing the period of the mechanical motions that cause the flexural waves, to correspond to one or more resonant frequencies of the interventional device when it is coupled to the mechanical motion mechanism and inserted into a patient's body.

The mechanical motion mechanism can be utilized to assume periodic positions that result in flexural wave transmission along one or more preselected axes when the mechanism is activated by driving forces set at one or more of the resonant frequencies of the interventional device. In addition, the driving forces can be effectively controlled by conventional feedback techniques to maintain the desired operation at the resonant frequencies.

The present invention recognizes that mechanical distortions of an interventional device that assume the form of flexural waves provide a series of Doppler shifts along the propagated flexural wave shape that are readily detected by highly sensitive color ultrasound imaging systems for improved imaging of the entire interventional device when it is within a body. In addition, by transmitting the flexural waves in axial modes under resonant frequency operation, a scanner of the ultrasound color imaging system can be exposed to Doppler shifts emanating from each of, e.g., X, Y and Z axial directions. Accordingly, the orientation between the interventional device and the scanner is not critical to the detection and accurate display of the interventional device. Moreover, the axial modes permit the inherent resonance of the device to be utilized for efficient axial mode operation resulting from wave generation at resonant frequencies.

It has also been observed that flexural waves of a particular axial mode do, to some extent, migrate beyond the axis of propagation. Thus, Doppler shifts are provided from positions of the interventional device that extend beyond the specific X, Y and Z axial positions. The migration phenomenon expands the detectability of the interventional device while maintaining the efficiency afforded by causing mechanical distortions via flexural waves transmitted during resonant frequency activation. The efficiency of operation is further enhanced by taking advantage of the micron sized distortion sensitivity of known color ultrasound imaging system. The undulations of the flexural waves transmitted to the interventional device need only be of a few microns in magnitude to permit high quality detection of Doppler shifts along the entire length of a device. The detected Doppler shifts can be used to generate and display a color image of the entire device within the grayscale image of surrounding tissues.

BRIEF DESCRIPTION OF THE FIGURES

FIG. 4 consists of FIGS. 4a, 4b and 4c showing various resonant frequency modes which are accommodated by the flexural wave preparation according to the present invention.

FIG. 5 comprises a series of figures, namely 5a, 5b, 5c and 5d depicting various drive systems to excite the mechanical motion mechanism illustrated in FIG. 3.

FIG. 8 is a series of diagrams including FIGS. 8a, 8b and 8c depicting various drive and sense mechanisms which can be employed in the feedback scheme depicted in FIG. 7.

DETAILED DESCRIPTION

Figure 2:
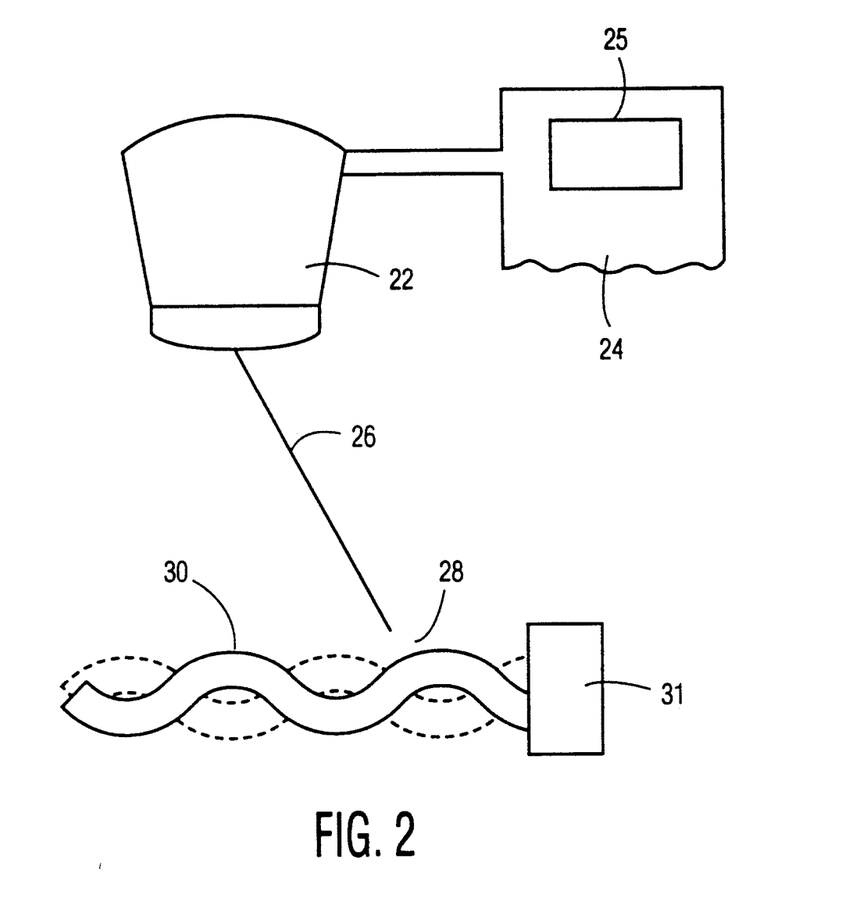
FIG. 2 is a pictorial representation of an ultrasound imaging system for transmitting mechanical motion to a cannula or other element according to the present invention.

As discussed above, FIG. 1 depicts relationships showing how blood velocity is measured in typical ultrasound systems. As is well known, such measurements can also be performed to detect the reciprocating motion or other motion of an interventional device such as a needle. Referring to FIG. 2, there is shown a simple block diagram representative of the operation of an exemplary embodiment of the present invention. FIG. 2 depicts an ultrasound imaging scan head 22 that is coupled to an ultrasound imaging system 24 having a display 25. The scan head 22 is shown impressing an imaging pulse 26 on a point of a vibrating element 30 such as an interventional device (displacement of the vibrating element 30 via phantom lines is exaggerated for clarity).

The interventional device can be, e.g., a needle. As an example of operation, the point 28 may be closest to the scan head 22 when the first imaging pulse 26 occurs and furthest when the second imaging pulse occurs. Known imaging systems 24 are able to detect and display the velocity of a moving element in the 1-100 centimeters per second or more (cm/sec) range. In order to accomplish this, the first and second imaging pulses 26 of FIG. 2 are produced typically every 80 to 330 microseconds ($\mu$sec) depending on the scale of the velocity to be detected. If a 5 cm/sec velocity is detected with a sampling interval of the imaging pulses set at 118 microseconds, the detected displacement of the point 28 is 5 centimeters/second times 118 microseconds, or approximately 6 microns. Therefore, as indicated above, small vibratory motions, on the order of microns, can be detected by known colorflow imaging systems.

As will be explained and referring to FIG. 2, a mechanical motion mechanism 31 according to the present invention is coupled to the needle 30. The mechanical motion mechanism 31 is capable of operating in at least one of a multiplicity of mechanical motion modes including modes able to transmit mechanical energy along one or more of the X,Y and Z axes of a device. According to the present invention, the mechanical energy produced by the mechanical motion mechanism 31 causes the transmission of mechanical energy in the form of flexural waves to the needle 30. As a result, the needle 30 undulates in flexural modes as depicted in FIG. 2 between the solid and phantom lines. In this manner, the needle 30 exhibits flexural vibrations in the X,Y and/or Z planes. Accordingly, the ultrasonic imaging system 24, via the scanner 22, can detect Doppler movements resulting from undulations of the flexural waves in any of the X, Y and Z planes and provide a precise indication on the display 25 as to the location of the needle 30 within a patient. To the contrary, as noted above in prior art techniques, the motion of a needle, to be detected and displayed, is a highly directional reciprocating motion along a longitudinal axis of the needle. Depending on how the scanning head is oriented relative to the needle, the reciprocating of the needle may entirely be missed or confused so that the practitioner will not know the exact positioning of the needle in relation to the body of the patient.

As indicated and as will be explained in conjunction with FIG. 3, the mechanical motion mechanism 31 operates in unique oscillatory modes to generate and transmit flexural waves along the needle 30. The term flexure as noted above, is utilized to denote the curving or bent state of the needle which is produced by the wave-like characteristics of the mechanical energy transmission generated by the mechanical motion mechanism 31. Flexure occurs in an elastic structural material when a deflection is suitable to set-up stresses in the material. The flexural waves are vibratory flexural waves which may operate and exhibit characteristics similar to standing waves or as propagating waves. The flexural waves provided by the mechanical motion generation are in one exemplary embodiment, transmitted about or along the X,Y and/or Z axes at synchronized, but non-harmonically related frequencies that correspond to resonant frequencies of the needle 30, as will further be explained.

Figure 3:
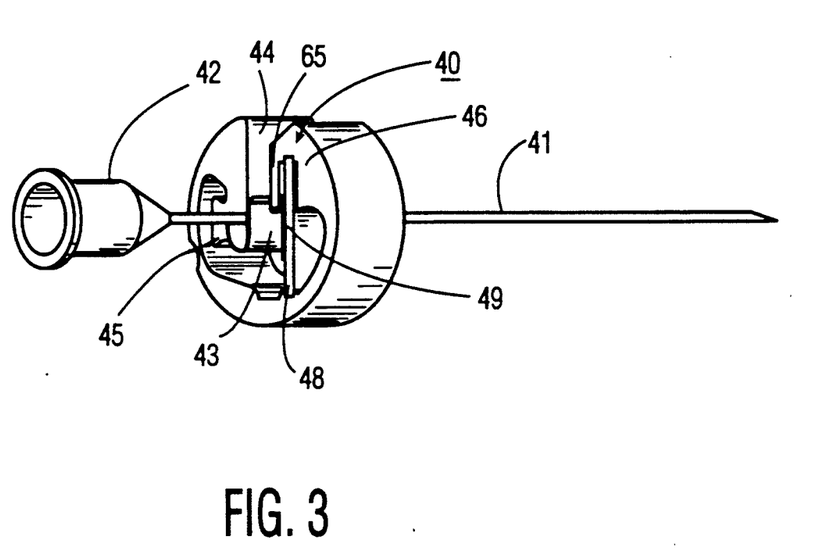
FIG. 3 is a planar representation of a mechanical motion mechanism coupled to a needle according to the present invention.

Referring now to FIG. 3, there is shown a needle or cannula 41 which is associated with a hub 42. The needle 41 is directed through and coupled to a mechanical motion mechanism according to an exemplary embodiment of the present invention and designated generally by the reference numeral 40. The mechanism 40 is constructed from a suitable metal material such as brass, zinc, stainless steel and alloys of the same. The term "VIBER" is a coined term used as a trademark by Echo Cath, Inc., the assignee herein, and is used to describe the vibratory mechanism 40. As one can ascertain, the mechanism 40 is formed to a generally C-shaped configuration having an elongated peripheral slot 44 which is bounded on one side by a pendulum-shaped member 45 and on the other side by a section 46 arranged to mount one or more plate-shaped piezocrystal diaphragms 48. At least one of the piezocrystal diaphragms 48 is activated or excited by means of a suitable voltage source as will be explained. For example, a metal electrode plate 49 can be utilized to couple the illustrated piezocrystal diaphragm 48 to a source of voltage.

As illustrated in FIG. 3 and FIG. 4, the VIBER mechanism 40 comprises a generally cylindrical or annular member having an internal hollow section of a relatively complex configuration designed to undergo various preselected motions, as will appear. The slot 44, as seen for example in FIG. 4, extends into the center of the annular shaped VIBER mechanism 40 towards a bottom curved surface. The slot is bounded on one side by the pendulum-shaped member 45 that includes a reduced neck portion and an end portion comprising a larger mass relative to the neck portion. The end portion of the pendulum-shaped member 45 together with the neck portion forms a pendulum like structure. As shown both in FIG. 3 and FIG. 4, there is also a downwardly extending depending wail 65 which serves to protect the piezocrystal diaphragm 48. The piezocrystal diaphragm 48 may be integrally formed with the VIBER mechanism 40 or may be a separate diaphragm, such as unimorph ceramic slab tightly coupled to the VIBER mechanism 40 by epoxy, glue, etc., and/or held in place by springing open the VIBER mechanism 40 and inserting the diaphragm 48 and thereafter allowing the frame to relax thereby tightly gripping the diaphragm 48 when the mechanism 40 returns to its relaxed position. The metal electrode plate 49 is coupled to the piezocrystal diaphragm 48 by glue, epoxy, welding and other suitable manner, but is offset from the center of the diaphragm 48.

A spring-like clip 43 is mounted to the pendulum-shaped member 45, as illustrated in FIG. 3. The clip 43 is used to secure the needle or cannula 41 to the VIBER mechanism 40. One of the advantages of the VIBER mechanism 40 is that it can be affixed to an any type of needle 41. As long as the means of affixing the needle is flexible, such as a spring wire metal clip 43, different needle gages can be secured by the clip 43. Current medical practices utilize needles of gages from 16 (1.6 mm diameter) to 25 (0.4 mm diameter) and of lengths from 0.5 inches to 10 inches, and also of many different style cutting tips. It is advantageous to provide a mechanism that is suitable for use with a variety of needles of different sizes and lengths. The VIBER mechanism 40, with its flexible clip 43, can be coupled to any particular needle even after the needle has been inserted into the body if visualization is then required. As one can see from FIG. 3, the diameter of the VIBER mechanism 40 is slightly larger than the diameter of the needle hub 42. It may be twice the diameter and so on, but in any event, it is designed as a relatively small and compact unit for convenient use during an interventional procedure. The circular outer peripheral surface of the VIBER mechanism 40 enables convenient manipulation of the combined mechanism/needle structure when directing the same through the interior of a body.

As indicated above, the VIBER mechanism 40 exhibits complex vibratory motion and essentially provides vibratory oscillations in the different planes (X,Y & Z). As will be explained, the VIBER mechanism 40 is vibrated by excitation of the plate-shaped piezocrystal diaphragm 48 resulting in the transmission of flexural waves to the coupled needle 41 via the clip 43. For example, a voltage of a preselected frequency can be applied to the piezocrystal 48 via electrodes such as the metal electrode plate 49. Due to the inherent properties or piezocrystal materials, the applied voltage causes the crystal to undergo mechanical vibrations as a function of the amplitude and frequency of the applied voltage. The mechanical vibrations of the piezocrystal diaphragm 48 periodically distort the shape of the VIBER mechanism 40 through various positions, also as a function of the amplitude and frequency of the applied voltage, resulting in the transmission of mechanical energy from the VIBER mechanism 40 to the needle 41, via the clip 43.

The VIBER mechanism 40 is designed to exhibit complex vibratory motions due to mechanical vibrations of the piezocrystal diaphragm 48 to controllably provide undulating oscillations at the clip 43 in different planes (e.g., X, Y & Z planes).

Experience indicates that the best color images are obtained at vibratory frequencies of ⅔ of ultrasound pulse repetition frequency, which for most commercial medical ultrasound instruments is indicative of vibratory frequencies of between 0.2 and 10 KHz. The mechanical resonance of the VIBER mechanism 40 amplifies the mechanical vibrations produced by the excited piezocrystal diaphragm 48, just as large excursions of a "swing" are the amplified effect of small pushes at the resonant rate of the swing. By operating the mechanism 40 at a resonant frequency of the mechanism 40 and attached needle 41, relatively small forces from the piezocrystal diaphragm 48 can be used to provide flexural wave transmissions to the needle 41 that result in mechanical motion of the needle 41 of sufficient magnitude for detection by known color ultrasonic imaging systems. It is indicated that while non-resonant operation of the VIBER mechanism 40 may also be used, such non-resonant operation does require stronger drive elements.

Figure 4A:
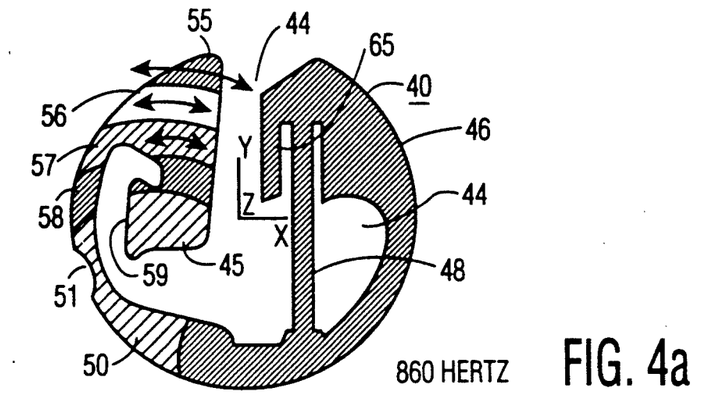
Figure 4B:
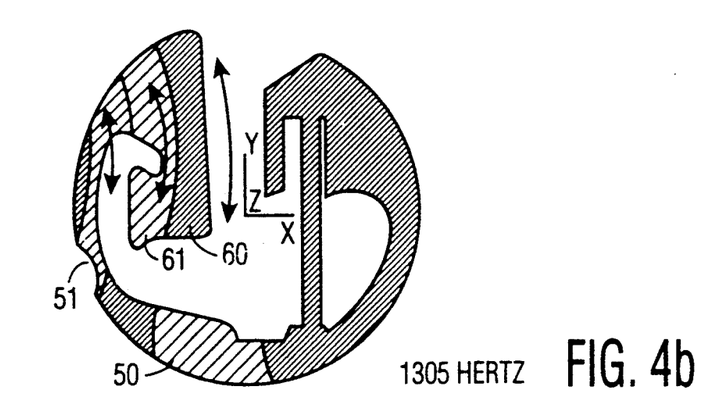
Figure 4C:
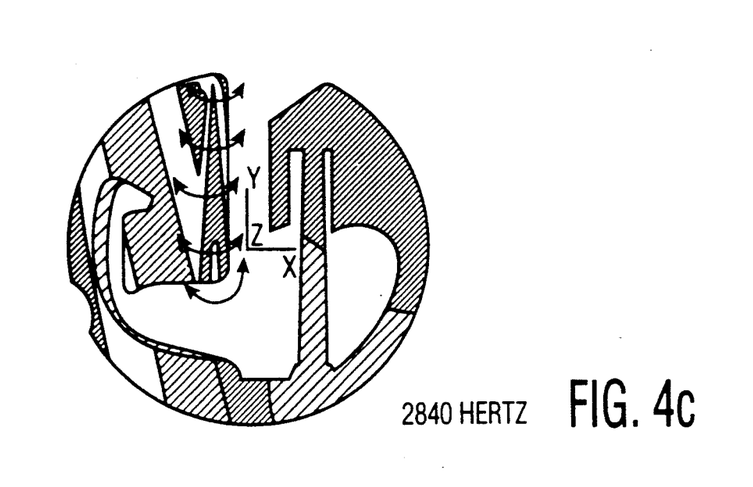

Referring now to FIG. 4, there is shown three views, namely 4a, 4b and 4c of the VIBER mechanism 40 as shown in FIG. 3, depicting three different modes of oscillations. In FIG. 4, there are various shades employed to illustrate the degree of movement of each of the shaded areas. Referring to FIG. 4a, there is shown a front plan view of the VIBER mechanism 40 including a small replica of an X, Y and Z set of axes in the center of the diagram. The left hand bottom of the VIBER mechanism 40 is characterized by an extending circular arm 50 having a reduced neck portion 51 which extends to and terminates in the pendulum-like member 45 with the relatively large bottom mass. The pendulum analogy is made based on the thinner neck portion with the relatively larger end portion. The member 45 is of a generally "L" shape cross-section used to reinforce oscillations caused by periodic distortion of the piezocrystal diaphragm 48, as described above.

As seen in FIG. 4a, there are a series of arrows associated with various regions along the pendulum-like member 45. The regions are depicted by the reference numerals 55, 56, 57, 58 and 59. Each region is depicted in a different shade with each shade being indicative of the extent of movement of one region with respect to other regions. The first operating mode, which is the lowest frequency of activation of the piezocrystal diaphragm 48 for the dimensions and material of the exemplary VIBER mechanism 40 depicted in FIG. 4a, is at 860 Hz. 860 Hz is a resonant frequency for the exemplary VIBER mechanism 40. In this mode, the pendulum-like member 45 is caused to oscillate by the 860 Hz distortion of the piezocrystal diaphragm 48 in the direction of the arrows, as from left to right and right to left, along the X axis. The amount of motion is a function of the shading whereby region 55 moves the most, region 56 moves more than region 57 which moves more than region 58, with region 59 which is analogous to the main mass concentration moving very little compared to the other regions. In as much as the clip 43 is mounted to the lower portion of the pendulum-like member 45, the oscillating motion along the X axis is transmitted to the needle 41 secured by the clip 43. The activating voltage applied to the piezocrystal diaphragm 48 at the resonant frequency of 860 Hz is sufficient to cause the X axis oscillation of the pendulum-like member 45 to transmit waves along the X axis of the needle 41.

In FIG. 4b, the resonant frequency of oscillation is 1305 Hz and the direction of the arrows again indicates the movement of the various shaded regions of the VIBER mechanism 40. As one can see, the movement depicted in FIG. 4b is mainly along the Y axis and the member 45 is moving up and down in the vertical plane or transverse to the X axis movement shown in FIG. 4a. The greatest movement occurs in region 60 with lesser movement in region 61 as shown in FIG. 4b.

Referring to FIG. 4c, there is shown the third oscillatory mode at a resonant frequency of 2840 Hz which basically is occurring about the Y axis or in directions of the Z axis. In the exemplary embodiment, the directions of the arrows indicate the relative movement which is a torque or twisting movement in and out of the plane of the paper. In this mode, the left side of the device is moving up and down (Y axis) and is also twisting in and out of the plane (Z axis) of the paper.

As should be understood, all of these modes can be achieved by driving the diaphragm 48 at an appropriate frequency. The frequency applied to diaphragm 48 need not be related to the oscillatory frequencies of FIG. 4a-4c. As indicated, these frequencies typically vary for ultrasound systems between 0.2 and 10 KHz. It is of course understood that there are other geometric forms which can be employed for the VIBER mechanism 40 so long as oscillating motions can be generated along preselected axis, as, e.g., the X, Y and Z areas of the structure used for the mechanical motion VIBER mechanism 40. The exemplary circular shape of the mechanism shown in FIG. 4a allows for easy mechanical machining and implementation. The device can also be changed in frequency modes by machining or changing the shape of the member 45 and thus obtaining different resonant frequencies.

The vibrator modes as depicted in FIGS. 4a, 4b and 4c can be generated simultaneously. Thus, based on these vibrational modes, the ultrasound imaging system can now detect Doppler changes in the X,Y and Z planes or in all planes which result in a marking on the display indicative of the exact location of the needle 41 receiving flexural waves from the VIBER mechanism 40. The dominant motion of any flexural wave may be along one axis perpendicular to the axis of the member which is carrying the flexural wave. Flexural waves will be produced at the ends of the structure such as next to the hub 42 of the needle or at bends in the structure where the bending moment of the flexural wave will have a component in the orthogonal axis, if it is desired that this polarization of the flexural wave be minimized, e.g., so that the physician does not need to worry about the rotational orientation of the VIBER mechanism 40 on the needle. Thus, one can excite different modes of resonance for the VIBER mechanism 40 whose dominant motions are on the orthogonal axes.

The modes depicted in FIG. 4 can be either sequentially or simultaneously excited to produce motions along all axes (X,Y and Z) of the flexural wave carrying needle 41. In any event, the twist mode as depicted in FIG. 4c may be used to affect both motions. It is of course understood that if these modes are implemented sequentially, it should be realized that the period of excitation of each mode should be long enough to build up the resonance of that mode, as for example approximately $Q \div \pi$ vibratory cycles, where Q is the measure of the ratio of the stored energy to the dissipated energy of a resonant structure. The concept of Q of course is well known in regard to vibratory modes.

Referring now to FIG. 5, there is shown several exemplary drive circuits for activating the piezocrystal diaphragm 48 of the VIBER mechanism 40. FIG. 5a depicts a bimorph piezoceramic crystal element for the diaphragm 48. As seen, the piezoceramic element is connected to a voltage source 69 and is excited at a particular frequency. As indicated, the frequency of excitation of the piezoceramic will cause the VIBER mechanism 40 to produce multiple modes of oscillation along the X,Y and Z axes. The frequencies are all synchronized even though they are not harmonically related. Piezoelectric devices to produce mechanical resonance are well known and many examples of such devices exist in the prior art.

Figure 5A:
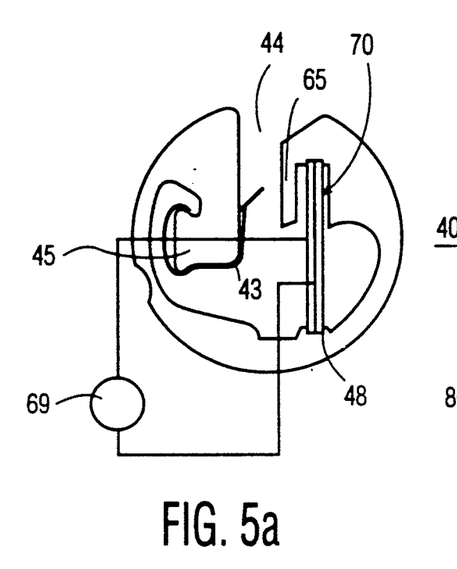
Figure 5B:
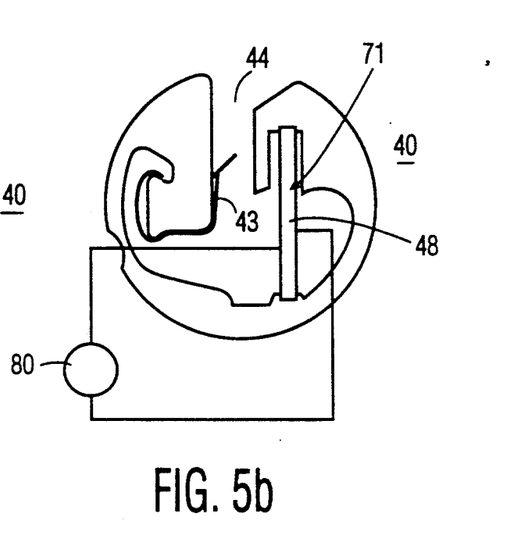

In this manner FIG. 5b depicts a piezoceramic or piezoelectric device 48 which is a unimorph device which again is activated by means of an oscillator circuit 80. The unimorph device 71 may be coupled to a suitable membrane or wall which may be constructed from brass or other materials to couple the vibratory modes of the piezoceramic device to the VIBER mechanism 40 or may be a simple slab piezoceramic driver that extends and contracts along its long axis when supplied with a varying voltage. As one can ascertain, piezoelectric ceramic devices such as ceramic unimorphs are used for both transmitters and receivers in telecommunication systems. The piezoelectric activity owes to an electrically polarized, synthetic ferroelectric ceramic. The flexural neutral axis of the composite structure is not at the ceramic's midplane; thus, vibration results in variation of the ceramic's diameter which induces a voltage across its thickness as defined through the piezoelectric constant. Such devices, as indicated, are well known, as is the entire field of piezoelectric transduction. In any event, such transducers are optimum devices to generate the frequencies required for excitation of the VIBER mechanism 40.

Figure 5C:
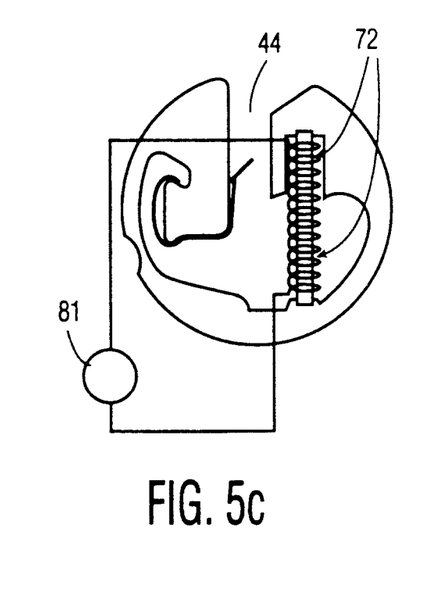

Referring to FIG. 5c, diaphragm 48 comprises a transducer 72 which, in turn, comprises a magnetic transducer. Such a magnetic transducer can again be energized or excited by means of an oscillator 81 to oscillate at the above-described frequencies.

Figure 5D:
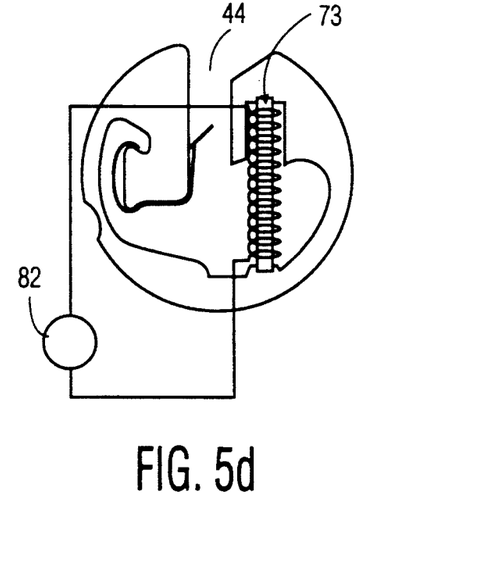

Referring to FIG. 5d, there is shown a diaphragm 48 that comprises a transducer 78 which uses a magnetostrictive effect. The transducer is excited by means of an oscillator 82. Magnetostrictive devices are also well known devices. Generally, magnetostrictive materials offer certain advantages for certain transducer applications.

Such devices, as well as piezoelectric ceramic materials have been utilized for underwater sound transducers. In case of piezoceramic transducers they are usually modified lead zirconate titanate (PZT) compositions and to a lesser extent modified barium titanate compositions. In the case of magnetostrictive materials, such materials employ nickel, Alfenol, Ferroxcube, Terfonal and other materials as well. The use of such materials is, as indicated, well known and common properties of such materials are well documented.

Another mode of operation of such a VIBER mechanism is that of pulsed excitation (FIG. 2), where the rate of the vibrating frequencies is several times of that of the frame rate of the scanner of the ultrasonic imaging system (which are typically 4 to 12 frames per second). This operation produces beads of color on the flexural wave carrying intervention device. These pulses of excitation must be wide enough to build up the resonance as above-described.

While the exemplary VIBER mechanism 40 has particular resonant frequencies determined by the shape of the mechanism and characteristics of the materials used to fabricate the mechanism, once the needle is affixed to the structure and placed in tissue, the resonant frequency is changed. As seen in FIG. 3, the needle 41 once coupled by the metal clip 43 to the VIBER mechanism 40 now produces a change in resonance frequency of the system due to a change in structure and mass. The change is relatively small as long as the needle mass is much less than that of the VIBER mechanism mass. This is normally the case. The VIBER mechanism 40 may be constructed from a suitable metal such as brass or stainless steel. The needle which may be stainless steel is an extremely thin tube or cannula with a very light needle hub 42. Thus, the mass of the VIBER mechanism 40 is much greater than the mass of the needle. In any event, the amount of the resonant frequency shift depends upon the mass, diameter and length of the needle and also upon the characteristics of the tissue in which the needle is inserted. A resonant mode is preferred for the system to obtain maximum amplitude vibrations. While the system can be tuned manually, it is of advantage to have a self adjusting system to automatically drive the VIBER mechanism member 40 with the optimal frequency and always near or at resonance.

Figure 6:
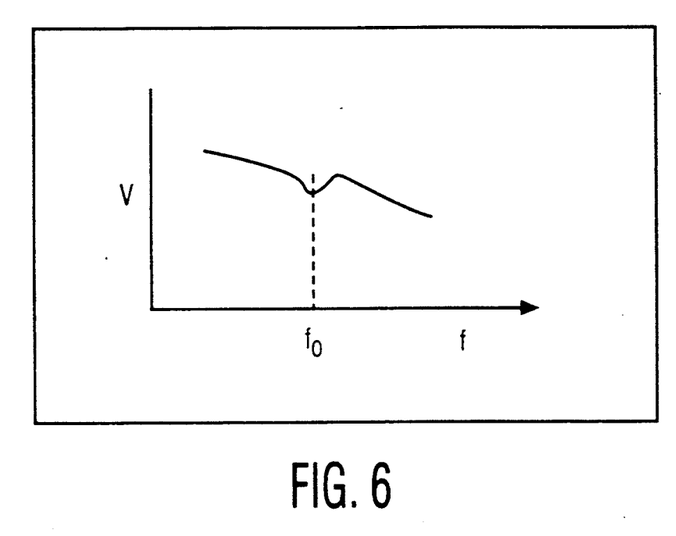
FIG. 6 is a graph depicting voltage vs. frequency response useful in describing the present invention.

Referring to FIG. 6, there is shown a typical example of voltage vs. frequency depicting a resonant frequency at $f_0$ which is characteristic of a dip which occurs in the driving waveform when a resonant frequency is achieved. This dip in voltage can be utilized or detected to determine the particular resonant frequency of the combined structure which includes the VIBER mechanism 40 and the needle or interventional medical device 41, as shown in FIG. 3. This dip in voltage is due to the back voltage generated by the motion of the structure. In the case of structures that utilize a piezoelectric plate when the VIBER mechanism 40 moves, a bucking voltage is generated by the piezoelectric effect. Similarly, when a magnetically driven structure is at resonance, the moving pole pieces will induce a back EMF in the coil that will cause a reduction in the voltage. In general, at resonance, the driving characteristics change. Thus, as one can ascertain, by monitoring the driving waveform as the frequency varies, resonance can be detected.

Figure 7:
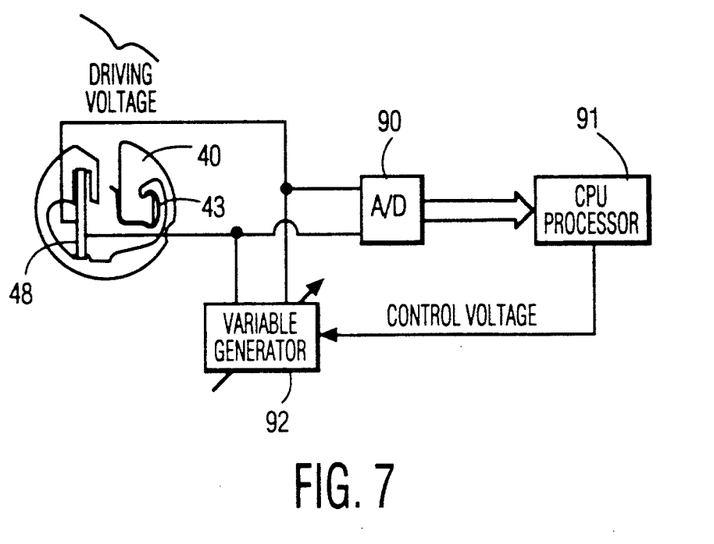
FIG. 7 is a block diagram showing a feedback based frequency control technique for supplying a drive voltage to the mechanical motion mechanism illustrated in FIG. 3.

Referring to FIG. 7, there is shown a circuit which operates to detect resonance and operates to automatically maintain the frequency used to drive the VIBER mechanism 40 system at resonance. As seen the VIBER mechanism 40 is shown with the clip 43 secured thereto and which clip is accommodating a needle as for example needle 41 of FIG. 3. In any event, there is shown a transducer drive element 48 which for example may be a piezoelectric ceramic device as shown for example in FIGS. 5a and 5b. The element 48 is coupled to a variable frequency generator 92 that can generate frequencies in the range between 2 to 10 KHz depending upon the medical ultrasound instruments being used. Within the above described frequency range, the variable generator 92 may produce a frequency range of between 2-3 KHz or between 9-10 KHz and again as a function of the particular ultrasound imaging system that is being employed. As indicated, most commercial medical ultrasound instruments contain means to detect vibratory frequencies between the above-described limits of 2 and 10 KHz.

The variable generator 92 provides a range of frequencies to the VIBER mechanism 40 by means of the piezoelectric or magnetic transducer 48. The drive leads as shown are coupled to the input of an analog to digital converter 90 which converts the analog drive voltage to digital signals at its output. The digital output is applied to the input of a CPU 91 or processor. The CPU 91 includes a microprocessor which analyzes the magnitude of the digital signals applied as the waveform of the oscillator 92 is varied. The oscillator 92 is varied by means of a control voltage which is applied by the processor 91 to a control terminal of the oscillator 92 to vary the frequency. The processor 91 analyzes the magnitude of the drive waveform as the oscillator 92 frequency is varied. In any event, by conventional feedback techniques, the oscillator frequency or the frequency utilized for driving the element 48 is forced to be at the frequency of resonance of the system. The resonant frequency is the entire resonant frequency of the system which includes the VIBER mechanism 40, the needle and the body tissue.

While the technique as shown in FIG. 7 provides operation that is reliable, there are other ways of controlling the frequency of the mechanism. Where there is a large dip in the drive waveform and where there is low noise in the measured waveform, in some situations a separate sensing element can be employed as part of the resonant structure.

Figure 8A:
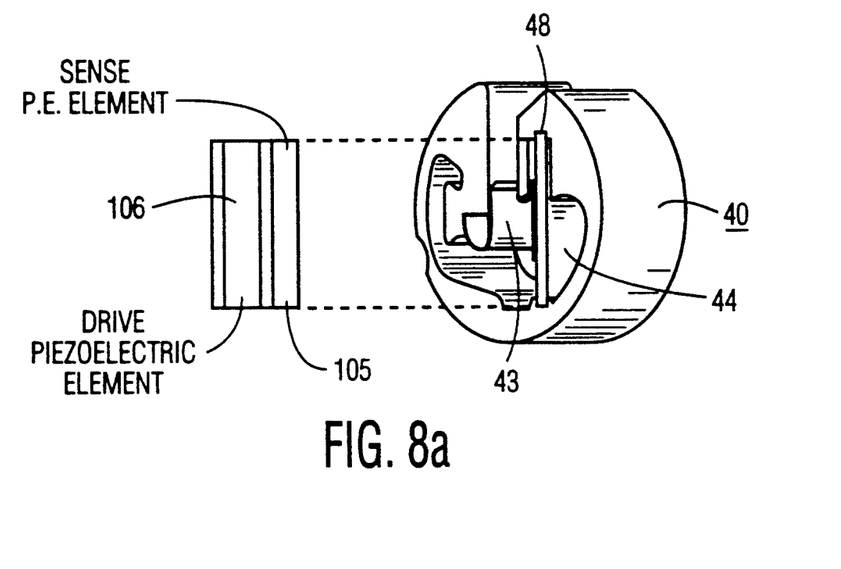

Referring to FIG. 8, there is shown various alternate devices where a separate sensing element is formed as part of the resonant circuit. In FIG. 8a, a sensing piezoelectric element is formed adjacent to the drive piezoelectric element. The sensing element depicted by reference numeral 105 is formed by conventional techniques and is located adjacent the drive element 106. In this manner, as the drive element receives driving voltages, the sensing element is energized by means of these driving voltages and enables a separate output to be provided. Thus, a separate piezoelectric element or alternatively a separate electrode on the driving piezoelectric plate will produce a characteristic change in voltage whose amplitude is related to the amount of motion and is a maximum at resonance. The peak in such a signal which is present in the output of the sense piezoelectric element 105 can easily be detected utilizing the feedback scheme as shown in FIG. 7. In these cases, the output of the sensing device is applied to the input of the A/D converter.

Figure 8B:
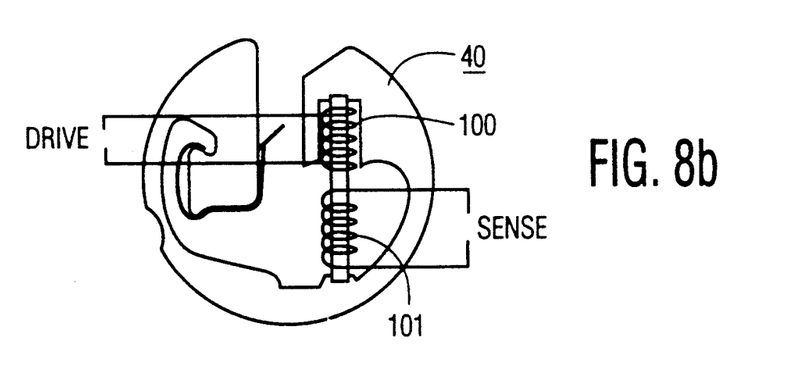

In FIG. 8b, there is shown a separate drive and sense coils which are associated which a magnetic drive circuit such as those shown in FIGS. 5c and 5d. In this manner, the drive coil 100 receives a drive voltage from the variable generator 92 of FIG. 7, while the sense coil detects and applies the voltage to the input of the A/D converter 90.

Figure 8C:
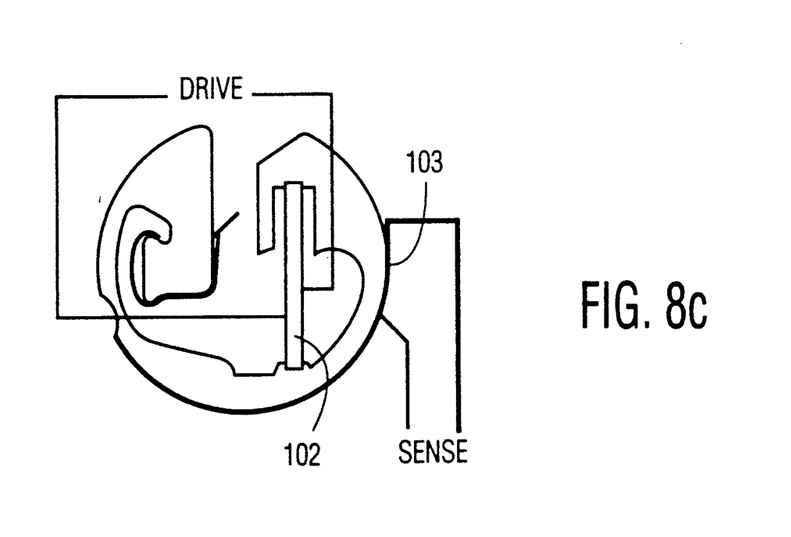

In FIG. 8c, there is shown a separate drive element 102 which may be a piezoelectric or other type of drive with a separate layer which is a PVF2 film 103 applied to the outer peripheral area of the VIBER mechanism 40. The film 103 operates as a sensing element with electrodes applied directly to the A/D converter 90 of FIG. 7. It is of course shown that with such sensors, as depicted in FIG. 8, it is also easy to measure and to display the amount of motion to be applied to the needle or other device to indicate to the user the exact amount of excitation.

Referring back to FIG. 7, the CPU 91 or processor is also programmed so that an individual ultrasound system having particular characteristics can be programmed to accommodate the particular mechanical motion mechanism being utilized. Thus, the frequency of operation of the variable generator 92 is a function of the particular system which is being utilized. The user, for example, will enter the name of the colorflow system in use and the CPU 91 is programmed to contain the specifications of the colorflow system so that it can display the proper settings for the needle detection, as for example the proper pulse repetition rate and the velocity colour map to be used for optimal visualization at the vibratory driving frequency. The resonant structure described can also be incorporated into alternate structures known as needle guides to guide needles along predetermined paths shown on the screen of the imaging system. Thus, a VIBER mechanism 40 which is built into a particular guide could add visualization to the present guiding functions. Hence, the use of flexural-waves to produce the small motions required to display the position of an interventional medical device in color for colorflow ultrasound imaging systems has many advantages. It is thus understood that the excitation of flexural waves in needles or other structures can be implemented by other means. In any event, one can employ end driven flexural waves developed on solid core guide wires and flexural waves can be produced on cannulas by driving the stylet so that different needle cannulae can be driven by a stylet equipped with a flexural wave driver. These drivers can be piezoelectric devices which can be incorporated to produce flexural waves in various other guiding systems.

Thus, many alternate embodiments, as well as additional embodiments will become apparent to those skilled in the art to enable the generation of flexural waves to enable the color ultrasound imaging system to respond to such waves to provide a indication to a physician or other user of the ultrasound system as to the location of the needle or other device to which the VIBER device is located on.

What is claimed is:

1. An ultrasonic imaging system for locating an interventional medical device within an interior region of a body under investigation, comprising:

a vibrator means coupled to said interventional medical device and operative to provide a vibratory mechanical oscillation along at least one axis at a frequency, to transmit said oscillation to said coupled medical device in the form of flexural waves, to cause said medical device to provide motion according to said flexual waves, and an ultrasonic imaging system including signal interrogation means for detecting said motion, and means for generating an image of said interior region of said body in which said motion and therefore said device is locatively represented.

2. The ultrasonic imaging system according to claim 1, wherein said at least one axis comprises X, Y and Z axes.

3. The ultrasonic imaging system according to claim 2, wherein the frequency of oscillation about each of said axes is different and harmonically non-related to one another.

4. The ultrasonic imaging system according to claim 1 further comprising exciting means coupled to said vibrator means for causing said vibrator means to mechanically oscillate.

5. The ultrasonic imaging system according to claim 4, wherein said exciting means comprises a piezoelectric transducer positioned on said vibrator means and operative when energized to cause said vibrator means to mechanically vibrate.

6. The ultrasonic imaging system according to claim 4, wherein said exciting means comprises magnetic means for causing said vibrator means to oscillate.

7. The ultrasonic imaging system according to claim 1, wherein said interventional device is a biopsy needle having a cannula with said vibrator means coupled to said cannula.

8. The ultrasonic imaging system according to claim 1, wherein said flexural waves are standing waves.

9. The ultrasonic imaging system according to claim 1, wherein said frequency is determined by said vibrator means, said interventional medical device and said interior body region and therefore varies accordingly with an amplitude of said oscillation being the greatest at resonance.

10. The ultrasonic imaging system according to claim 9, further comprising:

detection means coupled to said vibrator means and responsive to said frequency of vibration for providing a control signal according to said detected frequency, said control signal is of a predetermined magnitude at resonance, and controllable oscillator means coupled to said vibrator means for exciting said vibrator at the output frequency of said oscillator means, said oscillator having a terminal for receiving a signal, said signal determines said output frequency, and means for applying said control signal to said terminal, wherein said vibrator means varies frequency in accordance with the movement of said needle in said body as affecting said resonance in a direction to maintain vibrations at resonance.

11. A mechanism for transmitting mechanical motion to an interventional device, which comprises:

a wall structure;

an elastically deformable mounting element coupled to said wall structure for removably attaching said international device to said wall;

a drive element for creating controlled mechanical motion, mechanically coupled to said wall structure, wherein said wall structure undergoes preselected mechanical motions in response to said controlled mechanical motion of said drive element and wherein said preselected mechanical motions of said wall structure are transferred to said mounting element, thereby creating flexural mechanical waves in said interventional device.

12. The mechanism of claim 11, wherein the drive element comprises a piezocrystal material.

13. The mechanism of claim 11, wherein the drive element comprises a magnetic material.

14. The mechanism of claim 11, wherein the drive element comprises a magnetostrictive material.

15. The mechanism of claim 11, further comprising an electric drive circuit coupled to the drive element and operating at a preselected frequency to cause the controlled mechanical motion of the drive element.

16. The mechanism of claim 15, wherein the preselect frequency is a resonant frequency of the wall structure and the interventional device.

17. The mechanism of claim 11, wherein the wall structure comprises a C-shaped element having a peripheral slot dividing the C-shaped element into first and second portions; the drive element being connected to the first portion and the mounting element being connected to the second portion so that the controlled mechanical motion of the drive element causes the second portion to move along one or more of X, Y and Z axes to transmit flexural mechanical waves via the mounting element to one or more of X, Y and Z axes of the interventional device when the interventional device is coupled to the mounting element.

18. A method for use in conjunction with a color ultrasound imaging system for locating on a color image display of said system a medical device directed into a body, said system impressing ultrasonic imaging pulses on said medical device and detecting a Doppler shift in said imaging pulses reflected from said vibrating medical device, said Doppler shift being indicative of a change in displacement of said medical device and enabling said system to provide a color image on said display, comprising, the steps of:

generating said ultrasonic imaging pulses at a selected sampling frequency;

securing a vibrating means to said medical device, vibrating said medical device at a frequency to create flexural waves in said medical device with said vibrations being greatest at resonance with said vibrations creating said Doppler shift to enable said system to provide said color image on said display, detecting said frequency and amplitude of said vibrations, and applying a signal to said vibrating means to vary said vibrations according to said detected values to maintain said frequency near resonance independent of the position of said device on said body.

19. The method according to claim 18, wherein said vibratory frequency is about ⅜ of said sampling frequency or a non-multiple of said sampling frequency.

20. The method according to claim 19, wherein said vibrating means is a piezoelectric element.

21. The method according to claim 19, wherein said vibratory frequency is between 0.2–12 KHz.

22. The method according to claim 19, wherein said vibrating means is a magnetic element.

23. A method for transmitting mechanical motions to an interventional device, comprising the steps of:

providing a wall structure;

providing a drive element which causes preselected mechanical motions of said wall structure; and providing an elastically deformable mounting element for coupling said interventional device to said wall structure thereby causing said preselected mechanical motions of said wall structure to be transmitted to said interventional device as flexural mechanical waves.

* * * * *